United States Patent [19]

Henry et al.

[11] 4,112,217
[45] Sep. 5, 1978

[54] BIS-HYDRAZONES OF DAUNOMYCIN AND ADRIAMYCIN

[75] Inventors: David W. Henry, Chapel Hill, N.C.; George L. Tong, Cupertino, Calif.

[73] Assignee: SRI International, Menlo Park, Calif.

[21] Appl. No.: 830,091

[22] Filed: Sep. 2, 1977

[51] Int. Cl.² .............................................. C07G 3/00
[52] U.S. Cl. .......................................... 536/4; 536/17
[58] Field of Search .......................................... 536/4

[56] References Cited

U.S. PATENT DOCUMENTS

| | | | |
|---|---|---|---|
| 3,957,755 | 5/1976 | Jolles | 536/4 |
| 3,965,088 | 6/1976 | Jolles | 424/180 |

OTHER PUBLICATIONS

Jolles et al., Chemotherapy, vol. 8, Cancer Chemotherapy II, Plenum Press, New York and London (1975), pp. 237-241, (Chem. Abstracts 86:182689m).

*Primary Examiner*—Ethel G. Love
*Attorney, Agent, or Firm*—Donovan J. De Witt

[57] ABSTRACT

Bis-hydrazones of daunomycin and adriamycin having useful antitumor characteristics and the structure

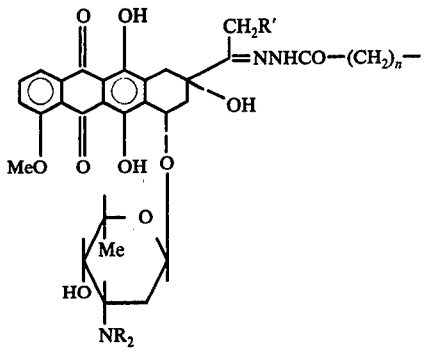

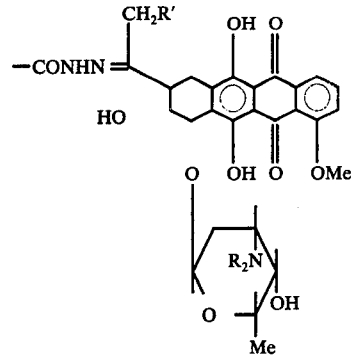

wherein $n$ is an integer having a value of from 0 through 8 and the radicals indicated by R and R' each represent hydrogen except that in those instances in which $n$ has a value of 2, the R groups, if not hydrogen, may be methyl radicals (with R' remaining as hydrogen), and the R' groups, if not hydrogen, may be hydroxy radicals (with R remaining as hydrogen).

11 Claims, No Drawings

BIS-HYDRAZONES OF DAUNOMYCIN AND ADRIAMYCIN

The invention described herein was made in the course of or under a contract with the U.S. Department of Health, Education, and Welfare.

| Representative compounds which fall within the scope of the present invention include: | |
|---|---|
| R=R'=H,n=2 | Bis(daunomycin) Succinylhydrazone Dihydrochloride (I) |
| R=R'=H,n=3 | Bis(daunomycin) Glutarylhydrazone Dihydrochloride (II) |
| R=R'=H,n=4 | Bis(daunomycin) Adipylhydrazone Dihydrochloride (III) |
| R=R'=H,n=6 | Bis(daunomycin) Suberylhydrazone Dihydrochloride (IV) |
| R=R'=H,n=8 | Bis(daunomycin) Sebacylhydrazone Dihydrochloride (V) |
| R=Me, R'=H,n=2 | Bis(N,N-dimethyldaunomycin) Succinylhydrazone Dihydrochloride (VI) |
| R=H,R'=OH,n=2 | Bis(adriamycin) Succinylhydrazone Dihydrochloride (VII) |
| R=R'=H,n=1 | Bis(daunomycin) Malonylhydrazone Dihydrochloride (VIII) |
| R=R'=H,n=0 | Bis(daunomycin) Oxalylhydrazone Dihydrochloride (IX) |
| R=R'=H,n=5 | Bis(daunomycin) Pimelylhydrazone Dihydrochloride (X) |

BACKGROUND OF INVENTION

The structures of the present invention represent a new class of doubly intercalating derivatives of daunomycin and adriamycin. Recent studies from several laboratories [especially that by Canellakis et al., Biophysica Acta, 418, 277–314 (1976)] have demonstrated that this mode of DNA binding is associated with important biological properties (especially cytotoxic and antitumor properties of a series of bis-9-acridyl compounds). Use of the helical DNA-adriamycin molecular model, which has proven useful in the past in this project, suggested that bis-derivatives of the type disclosed could form a unique doubly intercalated complex.

SUMMARY OF INVENTION

The present invention rests on discovery of novel compounds having useful antitumor characteristics which possess the following general structure

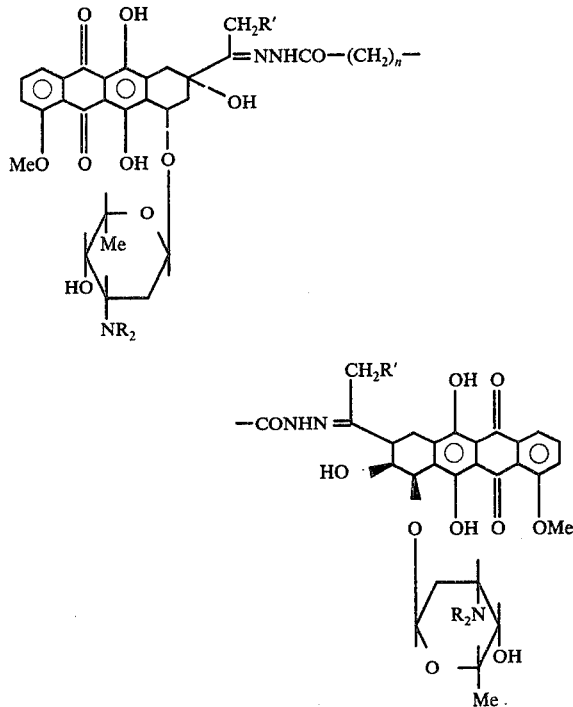

wherein $n$ is an integer having a value of from 0 through 8 and the radicals indicated by R and R' each represent hydrogen except that in those instances in which $n$ has a value of 2, the R groups, if not hydrogen, may be methyl radicals (with R' remaining as hydrogen), and the R' groups, if not hydrogen, may be hydroxy radicals (with R remaining as hydrogen), together with their pharmaceutically acceptable acid addition salts.

Compounds (I) through (X) enumerated above form the subject of corresponding examples 1 through 10, said examples including the details of the preparation of each compound as well as its characteristics. It will be noted that these compounds are prepared in the form of an acid addition salt with the free $NH_2$-or $N(CH_3)_2$-groups of the compounds. These acid addition salts (prepared as those of HCl) are preferably the pharmaceutically acceptable, nontoxic addition salts with suitable acids, such as those with inorganic acids, for example, hydrochloric, hydrobromic, nitric, sulphuric and phosphoric acids, and with organic acids, such as organic carboxylic acids, for example, glycolic, maleic, hydroxymaleic, malic, tartaric, citric, salicyclic acids, and organic sulphonic acids, for example, methanesulphonic and toluene-p-sulphonic acids.

The compounds are preferably employed in the salt form since they have adequate solubility in water. However, they can be employed in the non-acid condition.

An acid addition salt can be converted into the free compound according to known methods, for example, by treating it with a base, such as with a metal hydroxide or alkoxide, for example, an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid addition salt may also be converted into another acid addition salt by treatment with an anion exchange preparation.

In the treatment of cancer, the compounds of this invention or the salts thereof can be administered by any available route, including oral and parenteral (intravenous, intraperitoneal, subcutaneous, and intramuscular) administration. The amounts administered are those efficient to ameliorate the cancer.

Apart from requiring an extended reaction time, the compounds of this invention can readily be prepared by reacting the adriamycin or daunomycin starting materials (in suitable salt form) with the appropriate dihydrazide reactant, the reaction proceeding in an appropriate solvent (e.g., methanol) at room temperatures. Thus, when n is to have a value of 2 or 3, for example, the reactants employed are succindihydrazide and glutardihydrazide, respectively.

EXAMPLE 1

Bis(daunomycin) Succinylhydrazone Dihydrochloride (I)

A mixture of 1.13 g (2.0 mmol) of daunomycin hydrochloride (XII) and 0.146 g (1.0 mmol) of succinic acid dihydrazide in 120 ml of methanol was stirred at room temperature in the dark for three days. The reaction mixture was concentrated in vacuo to about 50 ml and then stirred at room temperature for two additional days. To the stirred solution was added 100 ml of ether dropwise; the resulting precipitate was collected, washed with ether and dried. The precipitate was powdered well and redried at room temperature /0.1 mm/16 hr to afford 1.18 g (91%) of (I) as an orange powder, mp decomposes slowly from 216°. IR (Nujol) 3.00, 3.10 $\mu$m (OH,NH), 5.95 C=N), 6.15, 6.29 (C=O, chelated quinone), UV-Vis max ($CH_3OH$) 233 nm ($\epsilon$ = 88,500), 250 sh (55,900), 288 (14,700), 477 (22,000), 495 (21,100), 531 sh (11,800). XL-100 NMR $DMSOd_6$ ($\sim$ 55°) 8.0–14.0 $\delta$ (v. broad, OH,$N^{\oplus}H_3$), 9.50 (bs, 2, NHCO), 7.81 (m, 4, H-1,3), 7.56 (m, 2, H-2), 5.32 (bs, 2, H-1'), 5.10 (s, 4, OH-4', 9), 4.90 (bs, 2, H-7), 4.12 ("d", 2, J=6Hz, H-5'), 3.96 (s, 6, $OCH_3$), 3.64 (bs, 2, H-4'), 3.38 (m, 2, H-3'), 2.98 (m, 4, H-10), 2.37 (bs, 4, $(CH_2)_2$), $\sim$ 2.37 (bs, 2, H-8B), 1.90 (s, 6, H-14), $\sim$ 1.85 (m, 2, H-8A), 1.80 (m, 4, H-2'), 1.18 (d, 6, J=6Hz, $CH_3$-5'). $[\alpha]_D^{21°}$ = +247° (c, 0.048, EtOH. Tlc on SiHF $CHCl_3/CH_3OH/H_2O$ (20/10/1 ), (XII) $R_f$ 0.40, (I) $R_f$ 0.04. Paper chromatography on Whatman No. 1 Paper: in n-BuOH/AcOH/$H_2O$ (5/2/3) (XII) $R_f$ 0.73, (I) $R_f$ 0.62; in n-PrOH/EtOAc/$H_2O$ (7/1/2) (XII) $R_f$ 0.67, (I) 0.07.

| Anal. Calcd. for $C_{58}H_{64}N_6O_{20}\cdot 2HCl\cdot 3H_2O$ | | | | |
|---|---|---|---|---|
| | C | H | $Cl^{\theta}$ | N |
| | 53.91 | 5.62 | 5.49 | 6.51 |
| Found: | 53.81 | 5.32 | 5.53 | 6.61 |

EXAMPLE 2

Bis(daunomycin) Glutarylhydrazone Dihydrochloride (II)

A mixture of 1.13 g (2.0 mmol) of daunomycin hydrochloride and 0.160 g (1.0 mmol) of glutaric dihydrazide in 120 ml of methanol was stirred at room temperature in the dark for 3 days. The reaction mixture was concentrated in vacuo to about 50 ml and then stirred at room temperature for two additional days. To the stirred solution was added 125 ml of ether dropwise; the resulting fine precipitate was collected, washed with ether and dried. The precipitate was powdered well and redried at room temperature /0.1 mm/16 hr to afford 1.20 g (93%) of (II) as an orange powder, mp 206°–220° dec. IR (Nujol) 2.98, 3.08 $\mu$m (OH,NH), 6.00 (C=N), 6.18, 6.31 (C=O, chelated quinone). UV-Vis max ($CH_3OH$) 233 nm ($\epsilon$ = 81,600), 250 sh (51,200), 290 (14,700), 484–492 plateau (19,800), 499 (20,100) 537 sh (11,600). XL-100 NMR $DMSOd_6$($\sim$ 50°) 9.0–12.0 $\delta$ (v. broad, OH,$N^{\oplus}H_3$), 9.89 (bs, 2, NHCO), 7.84 (m, 4, H-1,3), 7.60 (m, 2, H-2), 5.23 (bs, 2, H-1'), 4.95 (s, 2, OH), 4.87 (bs, 2, H-7), 4.12 (m, 2, H-5'), 3.98 (s, 6, $OCH_3$), 3.63 (bs, 2, H-4'), $\sim$ 3.3 (H-3', hidden by $H_2O$ peak), $\sim$ 3.1 (H-10B, hidden by $H_2O$ peak), 2.91 (d, 2, J=19Hz, H-10A), 2.23 (m, 8, H-8, $COCH_2CH_2CH_2CO$), 1.94 (s, 6, H-14) $\sim$ 1.94 (m, 2, $COCH_2CH_2CH_2CO$), 1.77 (m, 4, H-2'), 1.19 (d, 6, J=7Hz, $CH_3$-5'). $[\alpha]_D^{21}$ = + 166° (c, 0.052, EtOH). Tlc on SiHF $CHCl_3/CH_3OH/H_2O$ (20/10/1 ), (XII) $R_f$ 0.40 (II) $R_f$ 0.07. Paper chromatography on Whatman No. 1 Paper: in n-BuOH/AcOH/$H_2O$ (5/2/3) (XII) $R_f$ 0.73, (II) $R_f$ 0.66; in n-PrOH/EtOAc/$H_2O$ (7/1/2) (XII) $R_f$ 0.67, (II) $R_f$ 0.15.

| Anal. Calcd. for $C_{59}H_{66}N_6O_{20}\cdot 2HCl\cdot 2\frac{1}{2} H_2O$ | | | | |
|---|---|---|---|---|
| | C | H | $Cl^{\theta}$ | N |
| | 54.63 | 5.67 | 5.47 | 6.48 |
| Found: | 54.67 | 5.45 | 5.40 | 6.65 |

EXAMPLE 3

Bis(daunomycin) Adipylhydrazone Dihydrochloride (III)

A mixture of 0.316 g (0.56 mmol) of daunomycin hydrochloride and 0.049 g (0.28 mmol) of adipic acid dihydrazide in 25 ml of methanol was stirred at room temperature in the dark. After 5 days, the reaction mixture was concentrated to 13 ml and then 15 ml of ether was added dropwise. The resulting precipitate was collected, washed with 3–10 ml portions of ether and dried at room temperature /0.1 mm/15 hr to yield the bishydrazone dihydrochloride (III), 0.333 g (91%), mp - decomposes gradually 235°–250°. IR (Nujol) 2.82, 3.11 $\mu$m (OH), 5.98 C=O, hydrazone), 6.19, 6.31 (C=O, chelated quinone), UV-Vis max ($CH_3OH$) 233 nm ($\epsilon$ = 83,100), 250 sh (51,100), 289 (14,900), 479–488 plateau (20,300), 489–498 plateau (20,200), 535 sh (11,300). XL-100 NMR $DMSOd_6$ ($\sim$ 55°) 8-13 $\delta$ (v. broad, OH, $N^{\oplus}H_3$), 9.96 (s, 2, CONH), 7.80 (m, 4, H-1,3), 7.56 (m, 2, H-2), 5.35 (bs, 2, OH), 5.25 (bs, 2, H-1'), 5.04 (bs, 2, OH), 4.74 (m, 2, H-7), 4.12 (m, 2, H-5'), 3.97 (s, 6, $OCH_3$), 3.64 (bs, 2, H-4'), 3.40 (m, 2, H-3'), 3.22 (bs, $H_2O$), 2.98 (bs, 4, H-10), 2.30 (m, 8, H-8, $COCH_2(CH_2)_2CH_2CO$), 1.95 (s, 6, H-14), 1.80 (bs, 4, H-2'), 1.49 (bs, 4, $COCH_2(CH_2)_2CH_2CO$), 1.18 (d, 6, J=6Hz, $CH_3$-5'). $[\alpha]_D^{22°}$ = +247° (c, 0.047, EtOH). Tlc on SiGF in $CHCl_3/CH_3OH/2.0$ N AcOH (10/5/1) (XII) $R_f$ 0.56, (III) $R_f$ 0.30. Paper chromatography in n-PrOH/$H_2O$ (4/1) (XII) $R_f$ 0.63, (III) $R_f$ 0.30; in n-BuOH/AcOH/$H_2O$ (5/2/3) (XII) $R_f$ 0.75, (III) $R_f$ 0.69.

| Anal. Calcd. for $C_{60}H_{68}N_6O_{20}\cdot 2HCl\cdot 2\frac{1}{2} H_2O$ | | | | |
|---|---|---|---|---|
| | C | H | $Cl^{\theta}$ | N |
| | 54.96 | 5.77 | 5.41 | 6.41 |
| Found: | 55.02 | 5.48 | 5.19 | 6.30 |

EXAMPLE 4

Bis(daunomycin) Suberylhydrazone Dihydrochloride (IV)

A mixture of 0.406 g (0.72 mmol) of daunomycin hydrochloride and 0.073 g (0.36 mmol) of suberic acid dihydrazide in 70 ml of methanol was stirred at room temperature in the dark for 3 days. After concentrating to 35 ml, the reaction mixture was stirred at room temperature for an additional 8 days. To the stirred solution was then added 35 ml of ether dropwise; the resulting precipitate was collected, washed with 3–10 ml portions of ether and dried at room temperature /0.1 mm/18 hr to afford 0.407 g (85%) of the bis-hydrazone dihydrochloride (IV), mp 229°–232° dec. IR (Nujol) 2.82, 3.02 μm (OH), 5.99 (C=O, hydrazone), 6.20, 6.31 (C=O, chelated quinone). UV-Vis max (CH$_3$OH) 233 nm (ε = 85,300), 250 sh (53,500), 289 (15,300), 484–492 plateau (20,500), 498 (20,800), 535 (12,200). XL-100NMR DMSOd$_6$ (∼ 55°) 8–12 δ (v. broad, N$^⊕$H$_3$OH), 9.82 (s, 2, CONH), 7.80 (m, 4, H- 1,3), 7.59 (m, 2, H-2), 5.27 (bs, 2, H-1'), 5.17 (bs, 4, OH), 4.78 (bs, 2, H-7), 4.10 (m, 2, H-5'), 3.97 (s, 6, OCH$_3$), 3.64 (bs, 2, H-4'), 3.36 (m, 2, H-3'), 3.21 (d, 2, J=19Hz H-10B), 3.20 (bs, H$_2$O), 2.90 (d, 2, J=19Hz H-10A), 2.26 (m, 8 COC$\underline{H}_2$(CH$_2$)$_4$C$\underline{H}_2$CO,H-8), 1.93 (s, 6, H-14), 1.82 (bs, 4, H-2'), 1.35 (m, 8, COCH$_2$(C$\underline{H}_2$)$_4$CH$_2$CO), 1.18 (d, 6, J=6HzCH$_3$-5'). [α]$_D^{21°}$ = +273° (c 0.053, EtOH). Tlc on SiGF in CHCl$_3$/CH$_3$OH/2.0 N AcOH (10/5/1) (XII) R$_f$ 0.57, (IV) R$_f$ 0.34. Paper chromatography in n-PrOH/H$_2$O (4/1) (XII) R$_f$ 0.71, (IV) R$_f$ 0.44; in n-BuOH/AcOH/H$_2$O (5/2/3) (XII) R$_f$ 0.76, (IV) R$_f$ 0.68.

| Anal. Calcd. for C$_{62}$H$_{72}$N$_6$O$_{20}$·2HCl·2H$_2$O | | | |
|---|---|---|---|
| C | H | Cl$^⊖$ | N |
| 55.98 | 5.91 | 5.33 | 6.32 |
| Found: 55.96 | 5.75 | 5.28 | 6.27 |

EXAMPLE 5

Bis(Daunomycin) Sebacylhydrazone Dihydrochloride (V)

A mixture of 0.406 g (0.72 mmol) of daunomycin hydrochloride and 0.083 g (0.36 mmol) of sebacic acid dihydrazide in 165 ml of methanol was stirred at room temperature in the dark. At intervals, the reaction mixture was concentrated in the following manner: after 4 days to 70 ml, after 9 days to 35 ml, after 11 days to 21 ml, and after 28 days to 14 ml. After 35 days, an additional 0.008 g (0.036 mmol) of sebacic acid dihydrazide was added to the reaction mixture. After 42 days, the reaction mixture was diluted with 14 ml of ether added dropwise. The resulting precipitate was collected, washed with 5–10 ml portions of ether and dried at room temperature/0.1 mm/15 hr to give 0.419 g (87%) of the bis-hydrazone dihydrochloride (V), mp 211°–215° dec. IR (Nujol) 2.82, 3.14 μm (OH), 6.00 (C=O, hydrazone), 6.18, 6.30 (C=O, chelated quinone). UV-Vis max (CH$_3$OH) 234 nm (ε = 82,600), 250 sh (53,700), 288 (14,900), 481 (20,600), 488–497 plateau (20,400), 533 sh (11,900). XL-100 NMR DMSOd$_6$ (∼ 50°) 8–11 δ (v. broad, N$^⊕$H$_3$, OH), 9.86 (bs, 2, CONH), 7.79 (m, 4, H-1,3), 7.58 (m, 2, H-2), 5.28 (bs, 4, H-1', OH), 4.76 (m, 2, H-7), 4.07 (m, 2, H-5'), 3.95 (s, 6, OCH$_3$), 3.62 (bs, 2, H-4'), 3.37 (m, 2, H-3'), 3.20 (bs, 2, H-10B), 2.82 (d, 2, J=19Hz, H-10A), 2.21 (m, 8, H-8, COC$\underline{H}_2$(CH$_2$)$_6$C$\underline{H}_2$CO), 1.92 (s, 6, H-14), 1.82 (m, 4, H-2'), 1.19 (d, 6, J=6Hz CH$_3$-5'), 1.00 (bs, 12, COCH$_2$(C$\underline{H}_2$)$_6$CH$_2$CO). [α]$_D$ = +260° (c, 0.049, EtOH. Tlc on SiGF in CHCl$_3$/CH$_3$OH/2.0 N AcOH (10/5/1) (XII) R$_f$ 0.52, (V) R$_f$ 0.31. Paper chromatography in n-PrOH/H$_2$O (4/1) (XII) R$_f$ 0.71, (V) R$_f$ 0.56; in n-BuOH/AcOH/H$_2$O (5/2/3), (XII) R$_f$ 0.76, (V) R$_f$ 0.59.

| Anal. Calcd. for C$_{64}$H$_{76}$N$_6$O$_{20}$·2HCl·H$_2$O | | | |
|---|---|---|---|
| C | H | Cl$^⊖$ | N |
| 57.35 | 6.02 | 5.29 | 6.27 |

-continued

| Anal. Calcd. for C$_{64}$H$_{76}$N$_6$O$_{20}$·2HCl·H$_2$O | | | |
|---|---|---|---|
| C | H | Cl$^⊖$ | N |
| Found: 57.30 | 5.90 | 4.86 | 6.31 |

EXAMPLE 6

Bis(N,N-dimethyldaunomycin) Succinylhydrazone Dihydrochloride (VI)

A mixture of 0.374 g (0.6 mmol) of N,N-dimethyldaunomycin hydrochloride 1 3/4 hydrate and 0.0438 g (0.3 mmol) of succinic acid dihydrazide in 36 ml of methanol was stirred at room temperature in the dark for 2 days. After concentrating to 12 ml, the reaction mixture was stirred at room temperature for 5 additional days and then was diluted with 18 ml of ether added dropwise. The resulting precipitate was collected, washed with 3–10 ml portions of ether and dried at room temperature/0.1 mm/16 hr to yield 0.367 g (91%) of the bis-hydrazone (VI), mp 194°–196°. IR (Nujol) 2.98 μm (OH), 3.70 (HN$^⊕$(CH$_3$)$_2$), 5.98 (C=O, hydrazone), 6.18, 6.31 (C=O, chelated quinone). UV-Vis max (CH$_3$OH) 233 nm (ε = 89,900), 250 sh (56,700), 288 (15,400), 478 (22,200), 494 sh (21,200), 531 sh (11,800). XL-100 NMR DMSOd$_6$ (∼ 55°) 13.99 δ (s, 2, OH-6), 13.20 (s, 2, OH-11), 9.90 (bs, 2. HN$^⊕$(CH$_3$)$_2$), 9.74 (bs, 2, CONH), 7.79 (m, 4, H-1,3), 7.57 (m, 2, H-2), 5.57 (d, 2, J=6Hz, OH-4'), 5.41 (s, 2, H-1'), 5.15 (s, 2, OH-9), 4.91 (m, 2, H-7), 4.05 (m, 2, H-5'), 3.96 (s, 6, OCH$_3$), ∼ 3.9 (m, 2, H-3'), 3.40 (m, 2, H-4'), 3.21 (s, H$_2$O), 3.07 (bs, 2, H-10B), 2.87 (bs, 2, H-10A), 2.75 (s, 12, N$^⊕$(CH$_3$)$_2$), 2.30 (m, 8, H-8, COCH$_2$CH$_2$CO), 2.00 (m, 4, H-2'), 1.87 (s, 6, H-14), 1.19 (d, 6, J=6Hz, CH$_3$-5'). [α]$_D$ = +198° (c 0.051, EtOH). Tlc on SiGF in CHCl$_3$/CH$_3$OH/2.0 N AcOH (10/5/1) starting material R$_f$ 0.48, (VI) R$_f$ 0.28. Paper chromatography in n-PrOH/H$_2$O (4/1) starting material R$_f$ 0.78, (VI) R$_f$ 0.31; in n-BuOH/AcOH/H$_2$O (5/2/3) starting material R$_f$ 0.75, (VI) R$_f$ 0.66.

| Anal. Calcd. for C$_{62}$H$_{72}$N$_6$O$_{20}$·2HCl·3H$_2$O | | | |
|---|---|---|---|
| C | H | Cl$^⊖$ | N |
| 55.23 | 5.98 | 5.26 | 6.23 |
| Found: 55.06 | 5.74 | 4.87 | 6.27 |

EXAMPLE 7

Bis(adriamycin) Succinylhydrazone Dihydrochloride (VII)

A solution of 1.16 g (2.0 mmol) of adriamycin hydrochloride (XI) and 0.146 g (1.0 mmol) of succinic acid dihydrazide in 400 ml of methanol was stirred at room temperature in the dark. The reaction mixture was concentrated at intervals in the following manner: after 3 days to 200 ml, after 6 days to 100 ml, after 10 days to 50 ml, and after 14 days to 25 ml. After 22 days, an additional 0.015 g (0.1 mmol) of succinic acid dihydrazide was added to the reaction mixture. After 44 days, the reaction mixture was slowly diluted with 25 ml of ether; the resulting precipitate was collected, washed with ether and dried at room temperature/0.1 mm/15 hr to afford 1.22 g of (VII) containing 5–7% adriamycin hydrochloride (XI). A 0.608 g sample of crude (VII) in 10 ml of methanol was applied on a 2.5 × 90 cm (∼ 440 ml) column of Sephadex LH-20 (packed and washed with methanol). The column was eluted with methanol and 5.0 ml fractions were collected. Fractions No. 41–54 were combined and evaporated to yield 0.536 g of (VII). A second 0.607 g sample of crude (VII) was purified in a similar manner. The combined sample (0.961 g) of purified (VII) was dissolved in 20 ml of methanol and the solution was stirred and diluted with 20 ml of ether added dropwise. The resulting precipitate was collected, washed with 3–10 ml portions of ether and dried at room temperature/0.1 mm/20 hr to give 0.930 g (68%) of the bis-hydrazone dihydrochloride (VII), mp - gradually decomposes from 210°. IR (Nujol) 3.05 μm (OH), 6.00 (C=O, hydrazone), 6.18, 6.32 (C=O, chelated quinone). UV-Vis max (CH$_3$OH) 233 nm ($\epsilon$ = 86,000), 246 sh (59,400), 288 (15,800), 478 (21,900), 489 sh (21,200), 530 sh (11,700). XL-100 NMR DMSOd$_6$ (~ 55°), 8–12 δ (v. broad N$^\oplus$H$_3$, OH), 10.23 (bs, 2, CONH), 7.80 (m, 4, H-1,3), 7.55 (m, 2, H-2), 5.75 (bs, 2, OH), 5.31 (bs, 2, H-1'), ~ 5.3 (bs, 2, OH), 5.17 (bs, 2, OH), 4.91 (m, 2, H-7), 4.43 (bs, 4, H-14), 4.09 (m, 2, H-5'), 3.96 (s, 6, OCH$_3$), 3.63 (bs, 2, H-4'), 3.40 (m, 2, H-3'), 3.21 (s, H$_2$O), 3.05 (d, 2, J=19Hz, H-10B), 2.94 (d, 2, J=19Hz, H-10A), 2.31 (m, 4, H-8), 1.83 (m, 4, H-2'), 1.19 (d, 6, J=6Hz, CH$_3$-5'). [α]$_D$ = +232° (c 0.05, EtOH). Tlc on SiGF in CHCl$_3$/CH$_3$OH/H$_2$O (20/10/1), (XI) R$_f$ 0.32, (VII) R$_f$ 0.03; in CHCl$_3$/CH$_3$OH/2.0 N AcOH (10/5/1) (XI) R$_f$ 0.43, (VII) R$_f$ 0.17. Paper chromatography in n-PrOH/H$_2$O (4/1) (XI) R$_f$ 0.47, (VII) R$_f$ 0.05; in n-BuOH/AcOH/H$_2$O (5/2/3) (XI) R$_f$ 0.62, (VII) R$_f$ 0.56.

| Anal. Calcd. for C$_{58}$H$_{64}$N$_6$O$_{22}$·2HCl·5H$_2$O | | | |
|---|---|---|---|
| C | H | Cl$^\theta$ | N |
| 51.22 | 5.63 | 5.21 | 6.18 |
| Found: 51.21 | 5.27 | 5.13 | 6.36 |

EXAMPLE 8

Bis(daunomycin) Malonylhydrazone Dihydrochloride (VIII)

A solution of 0.339 g (0.6 mmol) of daunomycin hydrochloride and 0.0396 g (0.3 mmol) of malonyl dihydrazide in 24 ml of methanol was stirred in the dark at room temperature. After 14 days, the reaction mixture was concentrated to 12 ml and then 25 ml of ether were added dropwise. The resulting precipitate was collected, washed with 5—5 ml portions of ether and dried at room temperature /0.1 mm/16 hr to afford 0.351 g (93%) of the malonylhydrazone (VIII), mp dec. 225°–240°. IR (Nujol) 2.92 μm ( OH), 5.92 (C=N), 6.17, 6.31 (C=O, chelated quinone). UV-Vis max (CH$_3$OH) 234 nm ($\epsilon$ 75,200), 250 sh 848,400), 287 (12,900), 483 (18,400), 493–499 plateau (17,900), 535 sh (10,300). XL-100 NMR DMSOd$_6$ (~ 55°) 8–12 δ (v. board, OH, N$^\oplus$H$_3$), 10.15 (s, 2, CONH), 7.72 (m, 4, H-1,3), 7.47 (m, 2, H-2), 5.29 (bs, 2, OH), 5.21 (bs, 2, H-1'), 4.87 (bs, 2, OH), 4.75 (bs, 2, H-7), 4.10 (m, 2, H-5'), 3.95 (s, 6, OCH$_3$), 3.61 (bs, 4, COCH$_2$CO, H-4'), 3.37 (m, 2, H-3'), 3.23 (bs, H$_2$O), 2.83 (bs, 4, H-10), 2.19 (m, 4, H-8), 1.92 (s, 6, H-14), 1.77 (m, 4, H-2'), 1.13 (d, 6, J=6Hz, CH$_3$-5'). [α]$_D^{21°}$ = +230° (c 0.053, EtOH). Tlc on SiGF in CHCl$_3$/CH$_3$OH. 2 N AcOH (10/5/1/) (XII) R$_f$ 0.56, (VIII) R$_f$ 0.17. Paper chromatography in n-PrOH/H$_2$O (4:1): (XII) R$_f$ 0.56, (VIII) R$_f$ 0.09; in n-BuOH/AcOH/H$_2$O (5/2/3): (XII) R$_f$ 0.79, (VIII) R$_f$ 0.71.

| Anal. Calcd. for C$_{57}$H$_{62}$N$_6$O$_{20}$·2HCl·1½ H$_2$O | | | |
|---|---|---|---|
| C | H | Cl$^\theta$ | N |
| 54.72 | 5.40 | 5.67 | 6.72 |
| Found: 54.84 | 5.59 | 5.43 | 6.71 |

EXAMPLE 9

Bis-(Daunomycin) Oxalylhydrazone Dihydrochloride (IX)

A suspension of 0.564 g (1.0 mmol) of daunomycin hydrochloride and 0.059 g (0.5 mmol) of oxalyl dihydrazide in 200 ml of methanol was stirred at room temperature in the dark. After 15 days, the homogenous reaction mixture was concentrated to 100 ml and stirred at room temperature for an additional 40 days. The reaction mixture was concentrated to 50 ml and then 75 ml of absolute ethanol was added dropwise. The resulting fine gelatinous precipitate was collected by centrifugation (3000 X g); the precipitate was transferred to a fritted disc funnel and washed with 2—2 ml portions of absolute ethanol and with 5 ml of ether. After drying at room temperature, the precipitate was powdered well and redried at room temperature /0.1 mm/17 hr to afford 0.459 g (73%) of the bis-hydrazone dihydrochloride (IX), mp gradually dec. 220°–240°. IR (Nujol) 2.90, 3.04 μm (OH), 5.99 (C=O, hydrazone), 6.16, 6.29 (C=O, chelated quinone). UV-Vis max (CH$_3$OH) 233 nm ($\epsilon$ = 83,200), 249 (57,700), 284 sh (17,400), 478 (22,700), 496 (22,000), 531 sh (12,000). XL-100 NMR DMSOd$_6$ (~ 50°) 6-12 δ (v. broad, N$^\oplus$H$_3$, OH), 10.50 (bs, 2, CONH), 7.82 (m, 4, H-1,3), 7.63 (m, 2, H-2), 5.29 (bs, 4, H-1', OH), 4.89 (m, 2, H-7), 4.13 (m, 2, H-5'), 3.98 (s, 6, OCH$_3$), 3.61 (bs, 2, H-4'), 3.34 (m, 4, H-10B, H-3'), 3.18 (s, H$_2$O), 2.89 (d, 2, J=19Hz, H-10A), 2.20 (m, 4, H-8), 1.94 (s, 6, H-14), 1.80 (m, 4, H-2'), 1.17 ("bs," 6, CH$_3$-5'). [α]$_D^{21°}$ = +261° (c 0.046, CH$_3$OH). Tlc on SiGF CHCl$_3$/CH$_3$OH/2 N AcOH (10/5/1) (XII) R$_f$ 0.49, (IX) R$_f$ 0.20. Paper chromatography in n-PrOH/H$_2$O (4/1): (XII) R$_f$ 0.66 (IX) R$_f$ 0.02; in n-BuOH/AcOH/H$_2$O (5/2/3) (XII) R$_f$ 0.73, (IX) R$_f$ 0.68.

| Anal. Calcd. for C$_{56}$H$_{60}$N$_6$O$_{20}$·2HCl·2½ H$_2$O (1255.08) | | | |
|---|---|---|---|
| C | H | Cl$^\theta$ | N |
| 53.59 | 5.38 | 5.65 | 6.70 |
| Found: 53.56 | 5.51 | 5.45 | 6.44 |

EXAMPLE 10

Bis-(daunomycin) Pimelylhydrazone Dihydrochloride (X)

A mixture of 0.452 g (0.8 mmol) of daunomycin hydrochloride and 0.0753 g (0.4 mmol) of pimelyl dihydrazide in 50 ml of methanol was stirred at room temperature in the dark for 7 days during which time the bis-hydrazone (X) precipitated. The precipitate was collected, washed with 5-1 ml portions of methanol and with 3-5 ml portions of ether and dried at room temperature. The precipitate was powdered well and redried at room temperature /0.1 mm/17 hr to give 0.373 g (71%) of the bis-hydrazone (X), mp 239°–242° dec. IR (Nujol) 2.80, 3.08 μm (OH), 6.00 (C=O, hydrazone), 6.16, 6.29 (C=O, chelated quinone). UV-Vis max (CH$_3$OH) 233 nm ($\epsilon$ 85,800), 250 sh (54,200), 290 (16,200), 486 (21,300), 499 (21,400), 536 sh (12,300). XL-100 NMR DMSOd$_6$ (~ 50°) 8–12 δ (v. broad, N⊕H₃, OH), 9.81 (s, 2, CONH), 7.81 (m, 4, H-1,3), 7.58 (m, 2, H-2), 5.25 (bs, 4, H-1', OH), 5.15 (bs, 2, OH), 4.83 (m, 2, H-7), 4.10 (m, 2, H-5'), 3.96 (s, 6, OCH₃), 3.64 (bs, 2, H4'), 3.24 ("m," 4, H-3', H-10B), 3.19 (bs, H₂O), 2.81 ("d," 2, J=19Hz, H-10A), 2.25 (m, 8, H-8, COC$\underline{H}$₂(CH₂)₃C$\underline{H}$₂CO) 1.94 (s, 6, H-14), 1.81 (m, 4, H-2'), 1.32 (m, 6, COCH₂(C$\underline{H}$₂)₃CH₂CO), 1.19 (d, 6, J=6Hz, CH₃-5'). [α]$_D^{21°}$ = +239°(c 0.054, CH₃OH). Tlc on SiGF CHCl₃/CH₃OH/2 N AcOH (10/5/1) (XII) R$_f$ 0.50, (X) R$_f$ 0.23. Paper chromatography in n-PrOH/H₂O (4/1) (XII) R$_f$ 0.66 (X) R$_f$ 0.27; in n-BuOH/AcOH/H₂O (5/2/3) (XII) R$_f$ 0.73, (X) R$_f$ 0.68.

| Anal. Calcd. for C₆₁H₇₀N₆O₂₀·2HCl·1½ H₂O (1307.21) | | | |
|---|---|---|---|
| | C | H | Cl⁻ | N |
| | 56.05 | 5.78 | 5.42 | 6.43 |
| Found: | 55.89 | 5.47 | 5.36 | 6.47 |

BIOLOGICAL TESTS

Biological testing data for compounds of this invention as the HCl salts, as well as for adriamycin and daunomycin, are presented in the table given below. The compounds were tested first in cultured lymphoid leukemia L1210 cells for inhibition of nucleic acid synthesis by previously reported procedures. The analogs were then tested against lymphocytic leukemia P388 implanted in mice, under the auspices of the NCI and according to its protocols which use the increased survival time of treated mice compared to controls as the measure of antitumor efficacy.

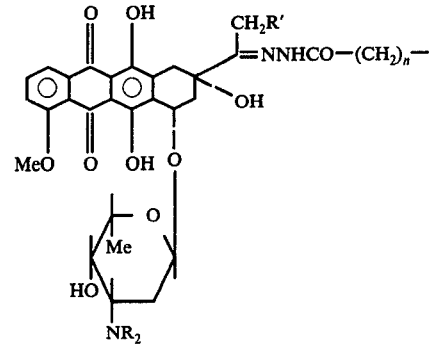

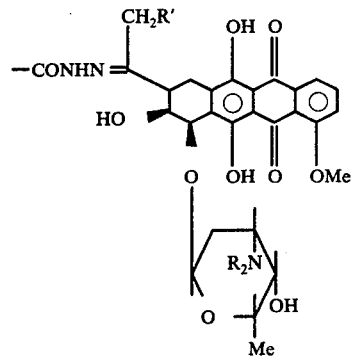

wherein $n$ is an integer having a value of from 0 through 8 and the radicals indicated by R and R' each represent hydrogen except that in those instances in which $n$ has

| | | Bioassay Data on Bis-hydrazones of Daunomycin and Adriamycin | | | | | |
|---|---|---|---|---|---|---|---|
| | | Vs Cultured L1210 Leukemia Cells[b] | | Vs P388 Leukemia in Mice[c] | | | |
| | | Inhibition of Synthesis | | Optimum | Antitumor | Optimum Dose | |
| | NSC[a] | of DNA | of RNA | Dose, qd 1-9 | Efficacy | q4d5,9,13 | Antitumor Efficacy |
| Compound | No. | ED₅₀, μM | Ed₅₀, μM | mg/kg | T/C, % | mg/kg | T/C,% |
| I | 266210 | 13 | 3.4 | 6.25 | 283[d] | 20 | 170 |
| | | | | 12.5 | 307[e] | | |
| II | 266211 | 4.5 | 3.6 | 1.56 | 188 | --no data-- | |
| | | | | 3.12 | 149 | | |
| III | 273432 | 8.9 | 3.6 | 6.25 | 281,289 | 37.5 | 196 |
| IV | 276747 | 4.9 | 2.4 | 8 | 245 | 25 | 178 |
| V | 276748 | 10 | 1.0 | 12.5 | 221 | 50 | 163 |
| VI | 274885 | 19 | 3.0 | 4 | 178 | 25 | 158 |
| VII | 273433 | 13.3 | 3.1 | 6.25 | 309 | 18.8 | 160 |
| VIII | 279510 | 14.1 | 7.4 | 6.25 | 169 | (inactive) | |
| IX | 285695 | 4.3 | 2.3 | | | 25 | 160 |
| X | 285696 | 2.0 | 1.3 | | | 25 | 160 |
| Adriamycin | 123127 | 1.5 | 0.67 | 1.0 | 195 | 8 | 157 |
| Daunomycin | 82151 | 0.49 | 0.39 | 0.5 | 166 | 8 | 134 |

[a]Accession number of the National Cancer Institute.
[b]Assay described in G. Tong, W. W. Lee, D. R. Black and D. W. Henry, J. Med. Chem., 19 395 (1976).
[c]Ip P388 murine leukemia treated ip on QD1-9 and Q4D 5, 9, 13 schedules according to standard NCI protocols. Assay described in R. I. Geran, N. H. Greenberg, M. M. MacDonald, A. M. Schumacker and B. J. Abbott, Cancer Chemother. Rep., Part 3, 3 (No. 2), 9 (1972), Protocol 1,200. T/C = ratio of survival time of treated mice to that of untreated controls times 100. Untreated controls survive about 9 days.
[d]Three out of six treated mice survived until sacrifice at 30 days.
[e]Two out of six treated mice survived until sacrifice at 45 days.

We claim:

1. Compounds having the structure a value of 2, the R groups, if not hydrogen, may be methyl radicals (with R' remaining as hydrogen), and the R' groups, if not hydrogen, may be hydroxy radicals (with R remaining as hydrogen), together with their pharmaceutically acceptable acid addition salts.

2. The compound of claim 1 in which is bis(daunomycin) succinylhydrazone together with its pharmaceutically acceptable acid addition salts.

3. The compound of claim 1 which is bis(daunomycin) glutarylhydrazone together with its pharmaceutically acceptable acid addition salts.

4. The compound of claim 1 which is bis(daunomycin) adipylhydrazone together with its pharmaceutically acceptable acid addition salts.

5. The compound of claim 1 which is bis(daunomycin) suberylhydrazone together with its pharmaceutically acceptable acid addition salts.

6. The compound of claim 1 which is bis(daunomycin) sebacylhydrazone together with its pharmaceutically acceptable acid addition salts.

7. The compound of claim 1 which is bis(N,N-dimethyldaunomycin) succinylhydrazone together with its pharmaceutically acceptable acid addition salts.

8. The compound of claim 1 which is bis(adriamycin) succinylhydrazone together with its pharmaceutically acceptable acid addition salts.

9. The compound of claim 1 which is bis(daunomycin) malonylhydrazone together with its pharmaceutically acceptable acid addition salts.

10. The compound of claim 1 which is bis(daunomycin) oxalylhydrazone together with its pharmaceutically acceptable acid addition salts.

11. The compound of claim 1 which is bis(daunomycin) pimelylhydrazone together with its pharmaceutically acceptable acid addition salts.

* * * * *